United States Patent
Bobrow et al.

(10) Patent No.: US 6,518,036 B1
(45) Date of Patent: Feb. 11, 2003

(54) METHOD OF PERMANENT FLUORESCENT ASSAY

(75) Inventors: Mark Norman Bobrow, Lexington, MA (US); Kevin Aaron Roth, Webster Groves, MO (US)

(73) Assignees: Nen Life Science Products, Inc., Boston, MA (US); Washington University, St. Louis, MO (US)

( * ) Notice: Subject to any disclaimer, the term of this patent is extended or adjusted under 35 U.S.C. 154(b) by 0 days.

(21) Appl. No.: 09/526,414

(22) Filed: Mar. 16, 2000

Related U.S. Application Data

(60) Provisional application No. 60/124,825, filed on Mar. 17, 1999.

(51) Int. Cl.$^7$ .................................................. C12Q 1/28
(52) U.S. Cl. ......................... 435/28; 562/450; 564/170
(58) Field of Search ................... 435/28, 968; 562/450; 564/170

(56) References Cited

U.S. PATENT DOCUMENTS

| | | | | |
|---|---|---|---|---|
| 4,950,588 A | * | 8/1990 | Dattagupta | 435/6 |
| 5,306,621 A | * | 4/1994 | Kricka | 435/7.91 |
| 5,407,806 A | * | 4/1995 | Yabuuchi et al | 435/25 |
| 5,863,748 A | * | 1/1999 | Bobrow | 435/28 |

FOREIGN PATENT DOCUMENTS

| | | |
|---|---|---|
| JP | 11-318492 A | 4/1995 |

OTHER PUBLICATIONS

Sanchez F. P–Phenol Derivatives as Enhancers of the Chemiluminescent Luminol HRP Peroxide Reaction. J of Luminescence 65(1)33–39, 1995.*
Diaz A. Hydrogen Peroxide Assay by Using Enhanced Chemiluminescence of the Luminol Peroxide HRP System. Analytica Chimica Acta 327(2)161–165, 1996.*
Diaz A. Phenol Derivatives as Enhancers and Inhibitors of Luminol Peroxide HRP Chemiluminescence. J Biolumin Chemilumin 13(2)75–84, 1998.*
Li, Y. Comparative Study of Some Synthesised and Commercial Fluorogenic Substrates for Horseradish Peroxidase and its Mimetic Enzyme Hemin by a Flow Injections Method. Analytica Chimica Acta. 1997, vol. 340, No. 1–3, pp. 159–168, especially p. 159 col. 2.
Tochacek, J. et al. Metal Containing Phenilic Antioxidants—Physical Behaviour and Efficiency of Stabilisation in Polypropylene. Polymer Degradation and Stability. Mar. 1990, vol. 27, No. 3, pp. 297–307.
Database Caplus, Accession No. 110:75071, CS 250990 B1, Preparation of [(dialkylhydroxyphenyl) propionamindo] kanoic acids and their salts as polymer stabilizers. Tochacek et al. Mar. 15, 1988.
Chao et al. (1996) Immunofluorescence signal amplification by the enzyme–catalyzed deposition of a fluorescent reporter substrate (CARD). Cytometry, 23:48–53.
Gross and Sizer (1959) The oxidation of tyramine, tyrosine, and related compounds by peroxidase. J. Biol. Chem. 234:1611–1614.
Guilbault et al. (1980) New substrates for the fluorometric determination of oxidative enzymes. Analytical Chemistry, 40(8):1256–1263.
Raap et al. (1995) Ultra–sensitive FISH using peroxidase–mediated deposition of biotin– or fluorochrome tyramides. Human Molecular Genetics, 4(4):529–534.
Speel et al. (1997) Sensitive multicolor fluorescence in situ hybridization using catalyzed reporter deposition (CARD) amplification. J. Histochem Cytochem., 45(10): 1439–1446.
Zaitsu and Ohkura (1980) New fluorogenic substrates for horseradish peroxidase: rapid and sensitive assays for hydrogen peroxide and the peroxidase. Analytical Biochemistry, 109:109–113.

* cited by examiner

*Primary Examiner*—Ralph Gitomer
(74) *Attorney, Agent, or Firm*—Gifford, Krass, Groh, Sprinkle, Anderson & Citkowski, P.C.

(57) ABSTRACT

A method for performing a peroxidase-based assay by reacting a peroxidase enzyme with a soluble organic p-hydroxyphenyl-containing compound having the formula:

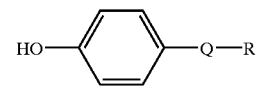

wherein Q is a linear or branched 1–12 heteroatom alkyl wherein the heteroatoms are selected from C, N, O, and S, wherein the bonds connecting the heteroatom alkyl chain are single or double, wherein any carbon atom in the heteroatom alkyl chain optionally includes a substituent selected from —OH, —COOH, —NH$_2$, and —SH, and wherein R is selected from —OH, —COOH, —NH$_2$, and —CH$_3$; and converting the soluble organic p-hydroxyphenyl-containing compound into a stable insoluble product which becomes highly fluorescent after illumination, upon excitation.

13 Claims, 5 Drawing Sheets

(5 of 5 Drawing Sheet(s) Filed in Color)

METHOD OF PERMANENT FLUORESCENT ASSAY

RELATED APPLICATION

This application claims priority of U.S. Provisional Application Serial No. 60/124,825 filed Mar. 17, 1999.

FIELD OF THE INVENTION

This invention relates to a method for a permanent fluorescent assay, and in particular, toward a fluorescent peroxidase-based assay utilizing a soluble p-hydroxyphenyl-containing substrate which forms an insoluble product through peroxidase activity.

BACKGROUND OF THE INVENTION

Horseradish peroxidase (HRP) (EC 1.11.1.7) is a commonly used enzyme label for immunological detection systems. HRP decomposes two molecules of hydrogen peroxide into water and oxygen. HRP initiates this reaction when it donates a pair of electrons to hydrogen peroxide. The enzyme subsequently extracts electrons (oxidizes) from a suitable donor.

Donor substrates for HRP and other enzymes which form soluble fluorescent products have been described. Gross and Sizer, J. Biol. Chem., 234: 1611–1614 (1959) describe the mechanism of the oxidation of tyramine and tyrosine by peroxidase. They found that the reaction products of tyramine and tyrosine with peroxidase are dityramine and dityrosine, respectively. In their analysis, they demonstrated the presence of new soluble fluorescent substances.

Guilbault, et al., Analytical Chemistry, 40 (8): 1256–1263 (1980) describe new substrates for the fluorometric determination of oxidative enzymes. In an attempt to improve the sensitivity of the colorimetric determination of carbohydrates, Guilbault et al. evaluated a series of phenolic peroxidase substrates in conjunction with the oxidation of the carbohydrates by either galactose oxidase or glucose oxidase. The phenolic substrates were chosen because they formed fluorescent solution phase products upon reaction with peroxidase and $H_2O_2$. The best substrates were found to be p-hydroxyphenylacetic acid, homovanillic acid, tyramine and tyrosine. In characterizing the oxidized fluorescent products, Guilbault et al. reported an excitation range of 315–326 nm and emission range of 410–425 nm for the group.

Zaitsu and Ohkura, Analytical Biochemistry, 109: 109–113 (1980) reported new fluorogenic substrates for horseradish peroxidase. They evaluated twenty-five p-hydroxyphenyl or 3-methoxy-4-hydroxyphenyl compounds for their suitability as soluble fluorogenic substrates for HRP. They concluded that 3-(p-hydroxyphenyl) propionic acid was the best substrate. For the fluorescent assay employed, the range of excitation wavelengths was 312 to 320 nm and the range of emission wavelengths was 400–422 nm.

Non-enzymatic fluorescent detection methods have been used in assays but they often suffer from poor sensitivity, and when sensitive enough, are not stable and do not allow for the archiving of results (Raap, et al., Human Molecular Genetics, 4 (4): 529–534 (1995); Speel, et al., J. Histochem. Cytochem., 45 (10): 1439–1446 (1997); Chao et al., Cytometry, 23: 48–53 (1996). One method for enhancing sensitivity is the use of enzymatic amplification. For peroxidase based solid phase assays, this is made difficult due to the lack of soluble non-fluorescent substrates which react to form insoluble fluorescent products. Thus, there is a need for such substrates in enzymatically amplified assays since they would allow for enhanced sensitivity and for archival storage and later use of assay results.

SUMMARY OF THE INVENTION

This invention relates to a method for a permanent, highly fluorescent peroxidase-based assay comprising reacting peroxidase with a soluble p-hydroxyphenyl-containing substrate which forms an insoluble, fluorescent product.

In another embodiment, this invention is directed to a peroxidase-based assay for detecting the presence or absence of a desired substance in a sample which may contain the desired substance, wherein the method comprises reacting a peroxidase enzyme with a soluble p-hydroxyphenyl-containing substrate that forms an insoluble, fluorescent product through peroxidase activity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Other advantages of the present invention will be readily appreciated as the same becomes better understood by reference to the following detailed description when considered in connection with the accompanying drawings wherein.

DETAILED DESCRIPTION OF THE INVENTION

Figure 1A:
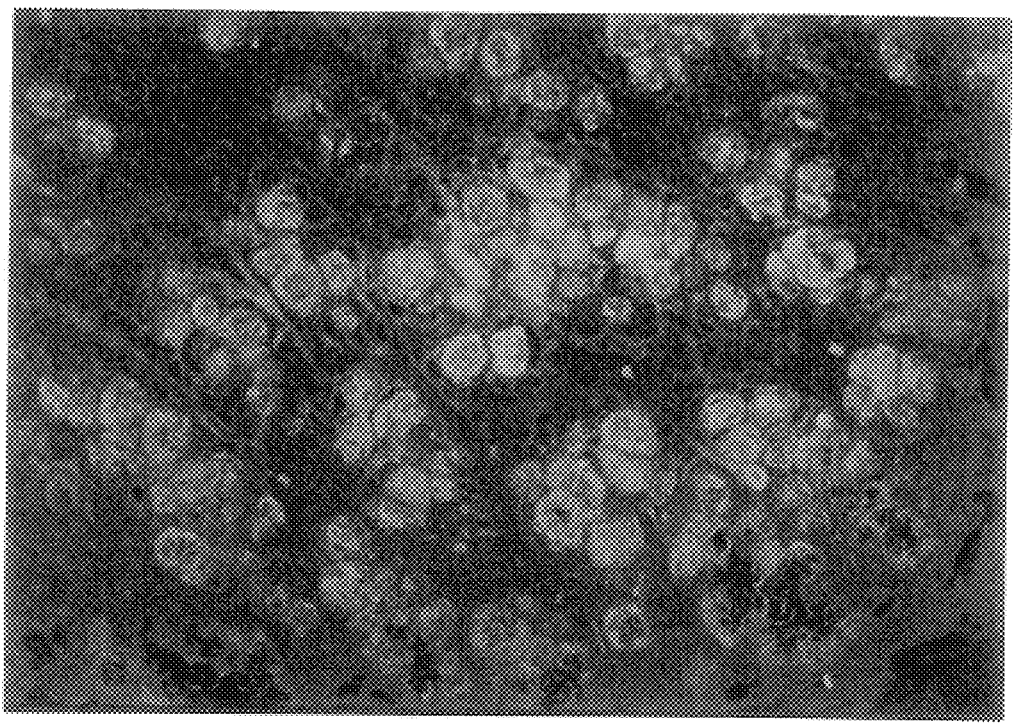
FIGS. 1A–F are photographs illustrating fluorescence detection on a tissue section utilizing a small p-hydroxyphenyl-containing HRP substrate wherein (A) is a photograph illustrating the fluorescent signal with 360 nm excitation using a blue-white filter set, (B) is a photograph illustrating the fluorescent signal following a one minute illumination at 360 nm using a blue-white filter set, (C) is a photograph illustrating the fluorescent signal following excitation at 490 nm using a green filter set, (D) is a photograph illustrating the same slide following a one minute illumination at 360 nm and excitation at 490 nm using a green filter set, (E) is a photograph illustrating the fluorescent signal following 550 nm excitation using a red filter set, and (F) is the same slide as shown in FIG. 1E following illumination for one minute at 360 nm and excitation at 550 nm utilizing a red filter set.

The term peroxidase based assay means a solid phase enzyme assay in which a peroxidase enzyme, such as HRP, is used as the enzyme label converting a soluble substrate to an insoluble product.

The term insoluble product means a product which precipitates out of the assay solution to form a solid which, generally, is deposited on a surface. Typical surfaces include, but are not limited to, cells or tissues, glass, plastic and silicon. It is to be understood that an "insoluble product" in accord with this invention may be soluble in some solvents; however, the product will be insoluble in the specific assay of the present invention.

The term p-hydroxyphenyl-containing means compounds containing the structure:

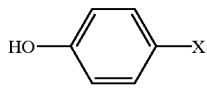

where X is a substituted aliphatic group.

More preferably, the p-hydroxyphenyl-containing compound has the structure:

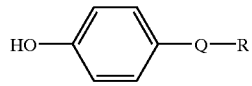

wherein Q is a linear or branched 1–12 heteroatom alkyl wherein the heteroatoms are one or more of C, N, O, and S, wherein the bonds comprising the heteroatom alkyl chain are single or double, wherein any carbon atom in the heteroatom alkyl chain optionally includes a substituent which may be —OH, —COOH, —NH$_2$, or —SH, and wherein R can be one or more of —OH, —COOH, —NH$_2$, or —CH$_3$. The soluble p-hydroxyphenyl-containing compound can be converted into a stable insoluble product which becomes highly fluorescent upon illumination.

Examples of p-hydroxyphenyl-containing substrates which can be used to practice the invention include:

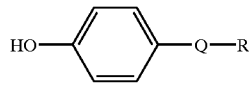

wherein Q-R is —(CH$_2$)$_2$CONH(CH$_2$)$_4$CH$_2$OH; —(CH$_2$)$_2$CONH(CH$_2$)$_5$CH$_2$OH; —(CH$_2$)$_2$CONH(CH$_2$)$_7$COOH; —(CH$_2$)$_2$COOH; —CH$_2$CH$_2$OH; —CH$_2$CH$_3$; —(CH$_2$)$_2$CH$_2$OH; or —(CH$_2$)$_2$CH$_3$.

Preferred p-hydroxyphenyl-containing substrates which can be used to practice the invention are:

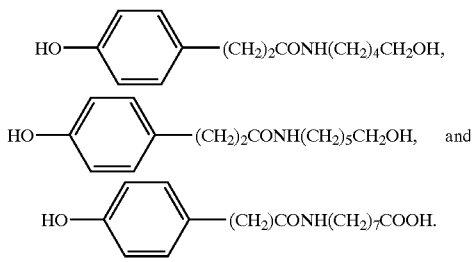

As used herein, the term substituted aliphatic can include a straight or branched chain hydrocarbon such as an alkyl group. Representative examples of alkyl groups are methyl, ethyl, propyl, isopropyl, isobutyl, butyl, tert-butyl, sec-butyl, pentyl, and hexyl.

The term "becomes highly fluorescent upon illumination" means that the insoluble product requires an initial activation by illumination at a wavelength of typically 300–400 nm which causes it to become highly fluorescent when subsequently excited. If the material is not first activated by illumination, the fluorescence, as described below, is very weak and barely visible, if at all. While not wishing to be bound by speculation, the inventors presume that activation creates a stable or metastable state in the material which enhances its fluorescence. The surprising and unexpected properties of the insoluble product may be due to the formation of a polymeric, crystalline, or dendrimer complex. The product can be formed by reaction of a suitable substrate with peroxidase, and subsequently used to label proteins, nucleic acids or other materials.

For example, for the p-hydroxyphenyl-containing substrates of the formula:

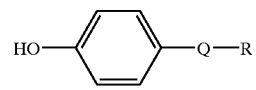

wherein Q-R is —(CH$_2$)$_2$CONH(CH$_2$)$_4$CH$_2$OH; —(CH$_2$)$_2$CONH(CH$_2$)$_5$CH$_2$OH; —(CH$_2$)$_2$CONH(CH$_2$)$_7$COOH; —(CH$_2$)$_2$COOH; —CH$_2$CH$_2$OH; —CH$_2$CH$_3$; —(CH$_2$)$_2$CH$_2$OH; or —(CH$_2$)$_2$CH$_3$, the initial illumination wavelength is less than 400 nm and typically ranges from approximately 340 to approximately 380 nm. Preferably, the illumination wavelength ranges from approximately 350 to approximately 370 nm. Clearly, other illumination wavelengths can be employed depending on the specific substrate utilized. One of ordinary skill in the art would be able to determine the appropriate wavelength for a given substrate.

After the initial illumination, the products exhibit surprising and unexpected fluorescence excitation and emission characteristics when subsequently illuminated. The unexpected characteristic is that the products exhibit fluorescence excitation/emission at multiple wavelengths. For example, the products can be excited at approximately 490 nm to produce a highly or brightly green fluorescence, viewed with an emission filter typically in the low 500 nm range. Further, the products can also be excited at approximately 550 nm to produce a highly or brightly red fluorescence, viewed with an emission filter typically in the high 570 nm range. Additionally, the products can be excited at wavelengths both above and below these ranges with concomitant emission characteristics. Thus, the fluorescence can be observed utilizing a multitude of excitation sources and fluorescent filters. If excited (e.g., at 490 or 550 um) to the point where fluorescence begins to fade, fluorescence is regenerated by illumination in the 360 nm range. Thus, the method of the invention overcomes the above-mentioned problems of the prior art by producing sensitive, stable and archivable fluorescent products. The emission characteristics also overcome problems of sample autofluorescence.

The method of the invention can be used with most solid phase assay systems using conventional technology well known to those skilled in the art in which peroxidase is used as the enzyme label such as for microarrays, histochemical assays, nucleic acid assays, immunoassays, etc. For histochemical assays or nucleic acid hybridization methods, the preferred surface is the medium itself, e.g., animal or plant cells and tissue affixed to a glass or plastic slide, membrane or bead.

The amount of substrate in the solution can vary over a considerable range depending upon the identity and concentration of the peroxidase enzyme whose activity is to be measured. The concentration can range from $1 \times 10^{-4}$M to $5 \times 10^{-2}$M. Preferably, the substrate is present in an amount from $1 \times 10^{-3}$M to $1 \times 10^{-2}$M. Clearly, other substrate concentrations can be utilized depending on the specific substrate and one of ordinary skill in the art could ascertain an appropriate substrate concentration.

The insoluble product is formed or developed by incubating the substrate solution with a sample containing the enzyme. Illumination of the insoluble product followed by excitation is a prerequisite for generating the fluorescence signal.

The instant invention includes a method for enhancing sensitivity in a peroxidase-based assay comprising reacting a peroxidase with a soluble p-hydroxyphenyl-containing substrate of the present invention to form archivable insoluble products which becomes highly fluorescent upon subsequent excitation.

It has been found, surprisingly and unexpectedly that the p-hydroxyphenyl-containing substrates form insoluble products which are not fluorescent or are weakly fluorescent, but which after illumination, and upon excitation become highly or brightly fluorescent. The products have a high degree of chemical stability, photostability, and fluorescence regeneration.

In another embodiment this invention is directed to a peroxidase-based assay for detecting the presence or absence of a substance in a sample suspected to contain the substance, wherein the improvement comprises reacting peroxidase with a soluble p-hydroxyphenyl-containing substrate that forms an insoluble product which becomes fluorescent after initial illumination and upon subsequent excitation. Such assays can be performed using conventional technology well known to those skilled in the art. Any type of antigen or nucleic acid can be detected using the present invention.

Experimental Data

EXAMPLE 1

Fluorescence Detection on a Tissue Section with a p-Hydroxyphenyl-containing HRP Substrate.

Sections of paraffin-embedded mouse intestine were deparaffinized, and non-specific binding sites were blocked by treatment for thirty minutes in PBS-blocking buffer (PBS-BB) (0.1 M phosphate buffered saline, pH 7.2; 1.0% bovine serum albumin, 0.2% non-fat powdered milk; and 0.3% Triton X-100). Horseradish peroxidase (HRP) conjugated wheat germ agglutinin (Sigma; St. Louis, Mo.) at a concentration of 10 $\mu$g/ml in PBS-BB was incubated on the sections for one hour at room temperature. Sections were then washed in PBS (three×five minutes each wash) and Tris (0.1 M Tris, pH 8.5; three×three minutes each wash). N-(5-hydroxypentyl)-3-(p-hydroxyphenyl) propionamide (HHPA), 1 mg/ml in Tris containing 0.003% $H_2O_2$, was then added to the sections at room temperature for ten minutes. Sections were then washed in Tris (three×three minutes each wash) and mounted with Tris:Glycerol (1:1) and coverslipped. Sections were viewed with a Zeiss Axioskop microscope equipped with epifluorescence and filter sets with excitation/emission characteristics of 360 nm/>400 nm (blue-white fluorescence); 490 nm/520 nm (green fluorescence); and 550 nm/570 nm (red fluorescence). Sections were photographed with a Zeiss MC100 camera system.

Figure 1B:
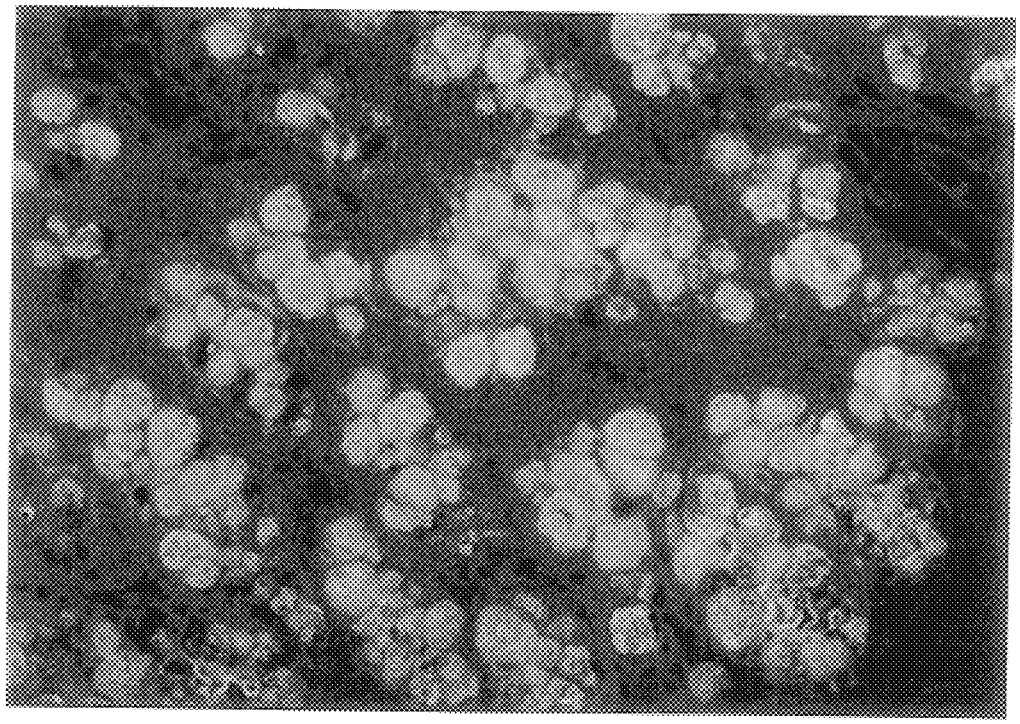
Figure 1C:
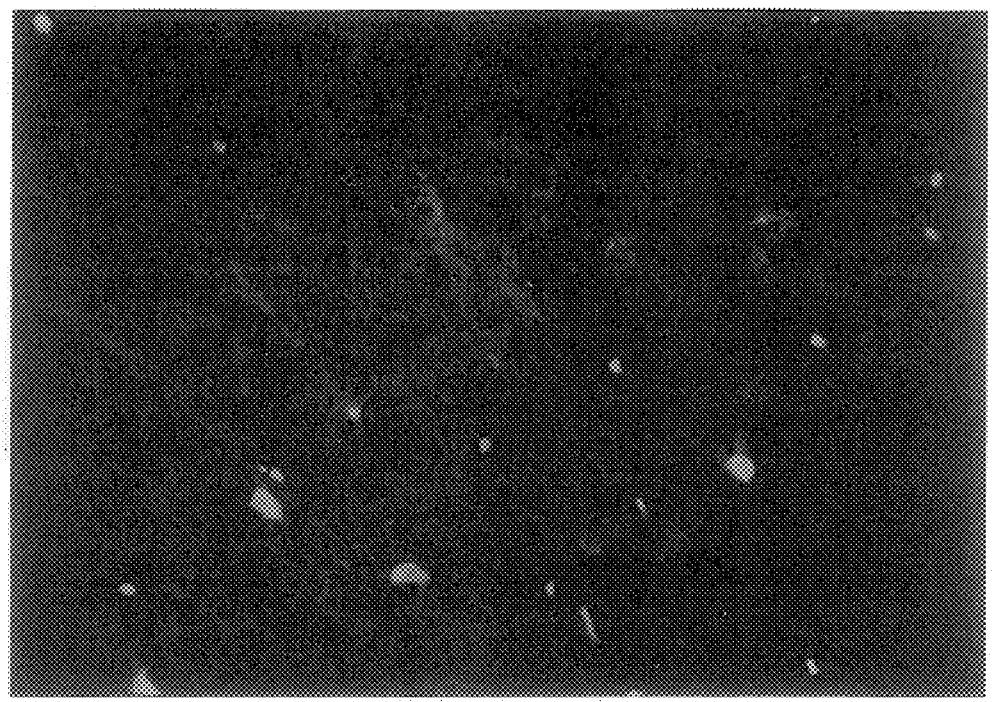
Figure 1D:
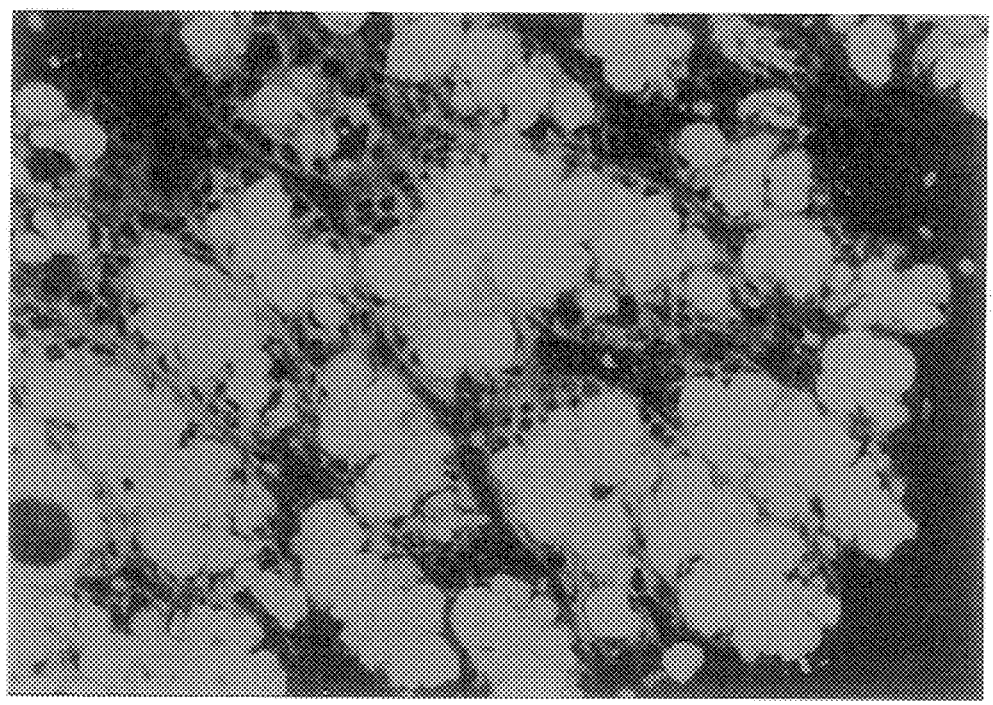
Figure 1E:
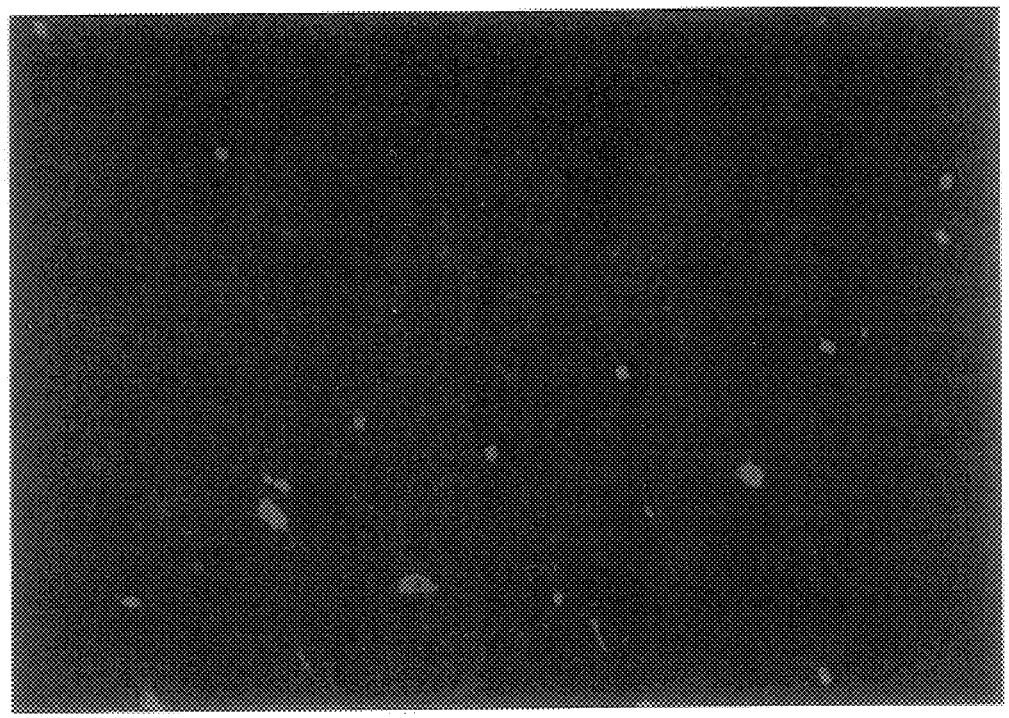
Figure 1F:
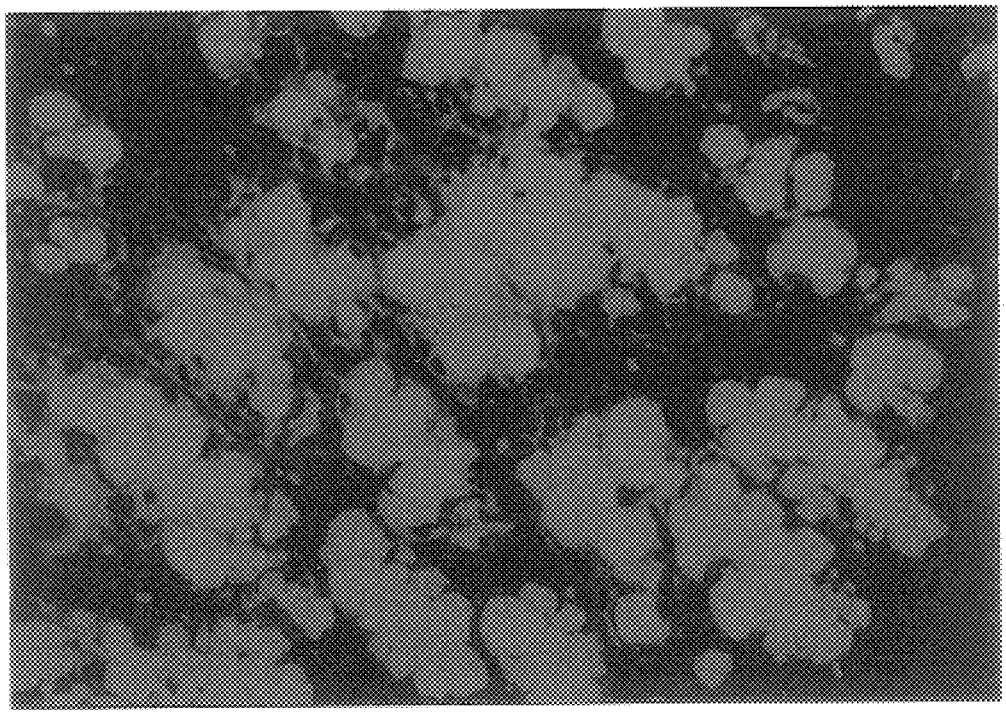

Wheat germ agglutinin binds to N-acetylglucosamine residues present in abundance in intestinal mucin producing goblet cells. Initial microscopic examination showed only weak fluorescence signal with 360 nm excitation (FIG. 1A, blue-white filter set) and almost no signal when viewed with either standard green (FIG. 1C) or red (FIG. 1E) filter sets. The microscopic field was then illuminated for one minute at 360 nm and reexamined as described above. There was a dramatic and unexpected increase in fluorescent signal following this brief exposure to 360 nm illumination. Intense fluorescent signals localized to goblet cells were now observed with all three filter sets, blue-white (FIG. 1B), green (FIG. 1D), and red (FIG. 1F). No goblet cell specific signal was observed in the absence of HRP conjugated wheat germ agglutinin incubation (data not shown). Original magnifications 400×.

EXAMPLE 2

Improved Fluorescent Signal Stability with a p-Hydroxyphenyl-containing HRP Substrate.

Sections of paraffin-embedded mouse brain were deparaffinized and non-specific binding sites were blocked by treatment for thirty minutes in PBS-BB. Monoclonal antibody against microtubule associated protein-2 (Sigma) was diluted 1:100,000 in PBS-BB and incubated on the sections overnight at 4° C. Sections were then washed in PBS (three×five minutes each wash) and incubated at room temperature for one hour with HRP-conjugated donkey anti-mouse antibodies (Jackson Immunoresearch Laboratories; West Grove, Pa.) diluted 1:1000 in PBS-BB. Sections were then washed in PBS (three×five minutes each wash) and microtubule associated protein-2 immunoreactivity was localized with either a TSA Direct Fluorescein kit according to the manufacturer's directions (NEN Life Science Products, Inc.; Boston, Mass.) or with HHPA (1 mg/ml in TSA amplification diluent for ten minutes). Sections were then washed in Tris (three×five minutes each wash), mounted in Tris:Glycerol (1:1) and coverslipped.

The fluorescein labeled section was viewed with a filter set having excitation/emission peaks at 490 nm/520 nm. The HHPA labeled section was first illuminated at 360 nm for one minute to activate the deposited reaction product and then viewed with a filter set having excitation/emission peaks at 360 nm/520 nm. Sections were viewed at time zero and after fifteen minutes of continuous excitation. Photomicrographs using standard two second exposures were taken at both time points to assess changes in fluorescence intensity over time. In addition, fluorescence intensity was semi-quantitated at both time points by recording the automatic exposure time required for photomicrographic documentation in a standard field using an ASA setting of 1600 and the MC100 camera system (Zeiss). Using this measure, short exposure times correlate with bright-fluorescence and long exposure times with dim fluorescence.

Figure 2A:
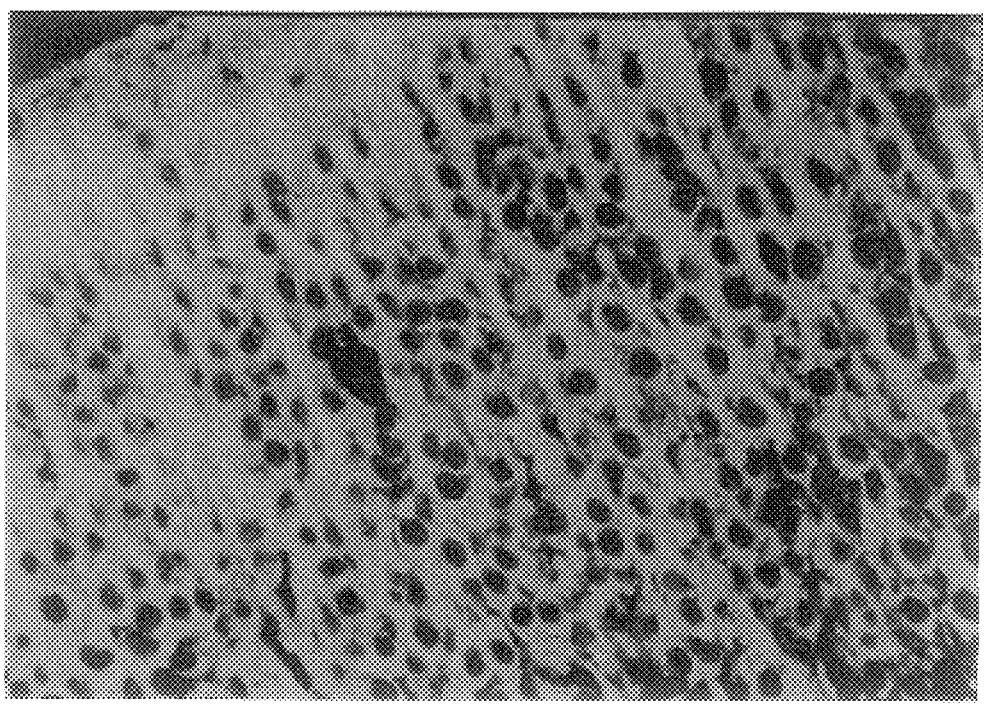
FIGS. 2A–D are photographs illustrating tissue sections wherein (A) is a tissue section reacted with TSA Direct-Fluorescein after initial excitation, (B) is the same section as in FIG. 2A following fifteen minutes of continuous excitation, (C) is a photograph of a tissue section reacted with HHPA after initial excitation and (D) is the same slide as in FIG. 2C following fifteen minutes of continuous excitation.
Figure 2B:
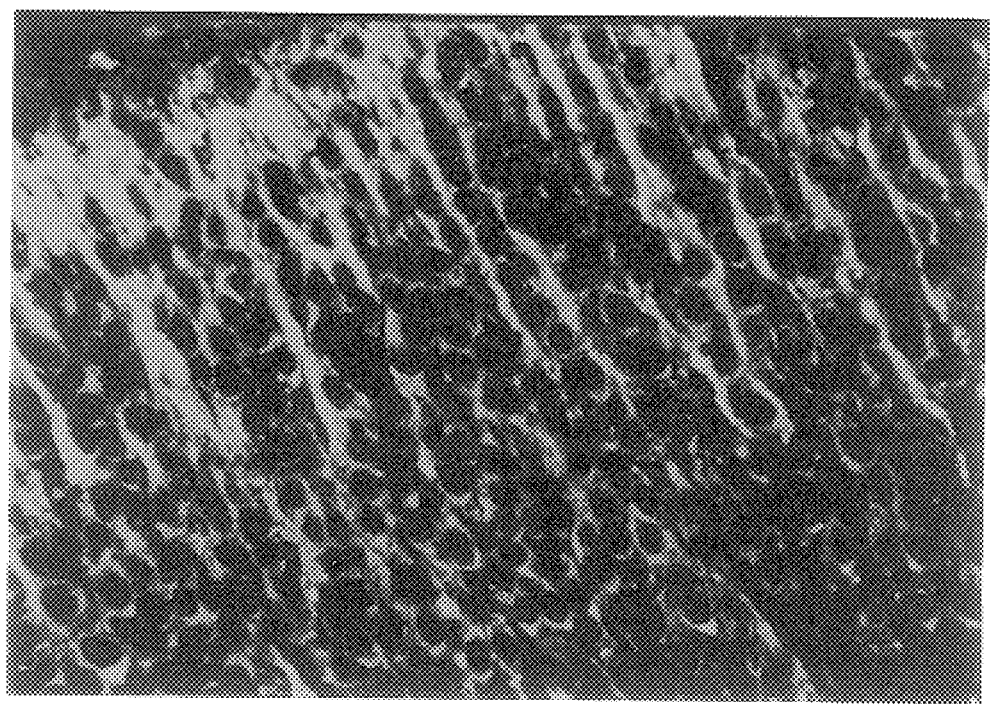
Figure 2C:
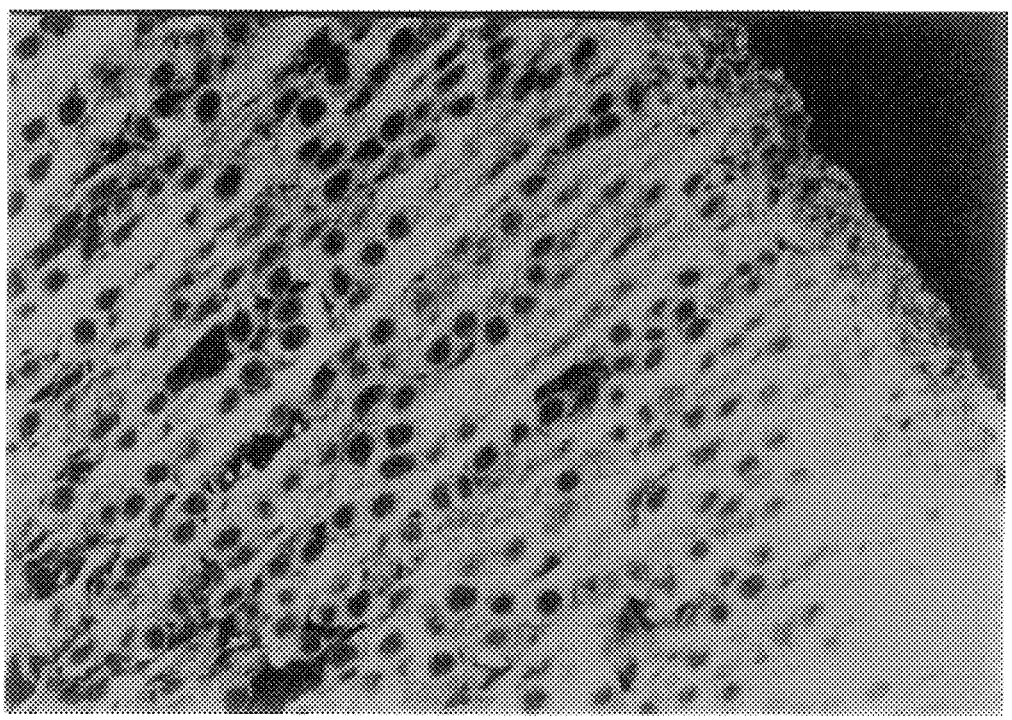
Figure 2D:
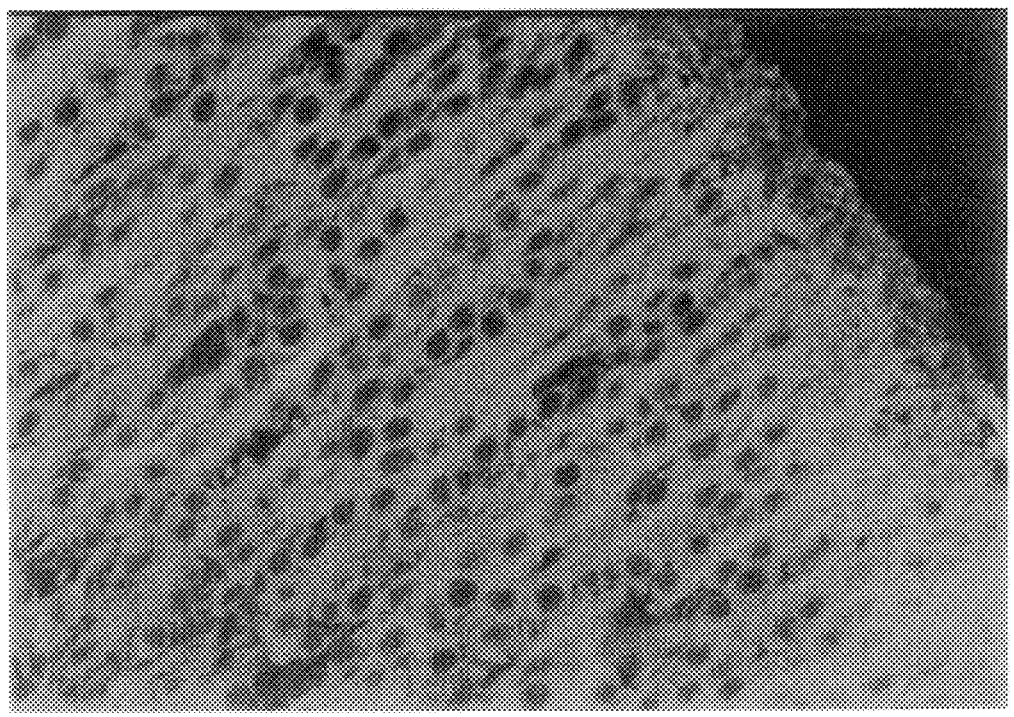

The section reacted with TSA Direct-Fluorescein showed a strong initial signal (FIG. 2A) which faded dramatically over the fifteen minutes of continuous excitation (FIG. 2B). The time required for a standard ASA 1600 exposure increased over six-fold from time zero (1.8 seconds) to fifteen minutes (12.0 seconds). In contrast, fifteen minutes of continuous excitation to the HHPA reacted slide resulted in increased fluorescence intensity (FIG. 2C, time zero; FIG. 2D, following fifteen minutes of excitation). Standard exposure time was decreased from 4.1 seconds to 3.1 seconds after fifteen minutes of constant excitation. This remarkable degree of fluorescence stability with HHPA was unexpected and unlike the typical loss of signal observed when most fluorophores are exposed to prolonged excitation. Original magnifications 60×.

The foregoing drawings, discussion and description are illustrative of the general principles of the present invention, and some specific embodiments thereof, but are not meant to be limitations upon the practice of the present invention, since numerous modifications and variations will be readily apparent to one of skill in the art. It is the following claims, including all equivalents, which define the scope of the invention.

What is claimed is:

1. A method for performing a peroxidase-based assay comprising:

reacting a peroxidase enzyme with a soluble p-hydroxyphenyl-containing substrate compound selected from the group consisting of:

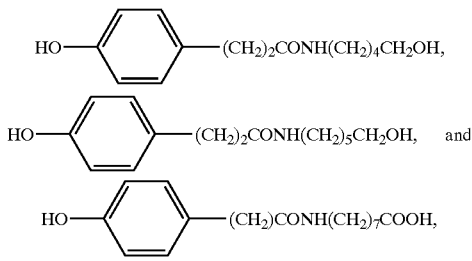

said substrate compound being further characterized in that after reaction with said peroxidase enzyme it forms an insoluble product which is characterized in that when it is illuminated it is converted to an activated form;

converting said insoluble product to an activated form by illuminating it with light;

illuminating said activated form of said insoluble product with light of a first wavelength so that said activated product fluoresces at a second wavelength which is longer than said first wavelength; and detecting said second wavelength.

2. A method according to claim 1, wherein the peroxidase enzyme is horseradish peroxidase.

3. A method according to claim 1, wherein the concentration of the substrate compound ranges from approximately $1\times10^{-4}$ M to $5\times10^{-2}$ M.

4. A method according to claim 3, wherein the concentration of the substrate compound ranges from approximately $1\times10^{-3}$ M to $1\times10^{-2}$ M.

5. A method according to claim 1 wherein the step of activating the insoluble product by illuminating it with light comprises illuminating it with light having a wavelength between approximately 340 nm to approximately 380 nm.

6. A method according to claim 5, wherein said light has a wavelength between approximately 350 nm to approximately 370 nm.

7. A peroxidase-based assay method for detecting the presence or absence of a desired substance in a sample, said method comprising the steps of:

reacting a peroxidase enzyme with a soluble p-hydroxyphenyl-containing substrate, said substrate compound being selected from the group consisting of:

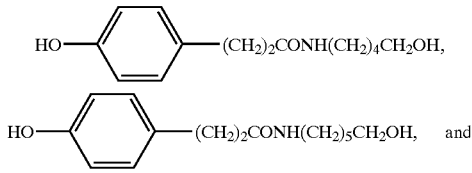

-continued

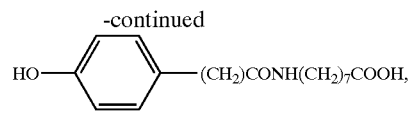

said substrate compound being further characterized in that after reaction with said peroxidase enzyme it forms an insoluble product which is characterized in that when it is illuminated it is converted to an activated form;

converting said stable, insoluble product to an activated form by illuminating it with light;

illuminating said activated form of said insoluble product with light of a first wavelength so that said activated product fluoresces at a second wavelength which is longer than said first wavelength; and detecting said second wavelength.

8. An assay according to claim 7, wherein the concentration of the substrate ranges from approximately $1\times10^{-4}$ M to $5\times10^{-2}$ M.

9. An assay according to claim 7, wherein the concentration of the substrate ranges from approximately $1\times10^{-3}$ M to $1\times10^{-2}$ M.

10. In a peroxidase-based assay of the type wherein a peroxidase enzyme is reacted with a substrate, the improvement comprising in combination: said substrate being a p-hydroxyphenyl-containing substrate selected from the group consisting of:

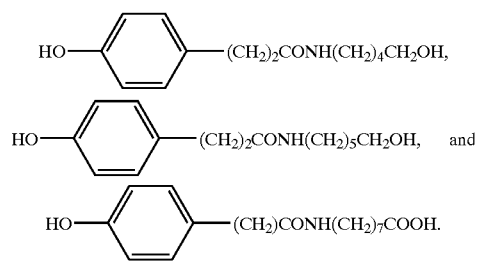

11. The assay of claim 10, wherein said substrate is initially present in solution, and wherein the improvement further comprises:

reacting said substrate compound with said peroxidase so as to produce a stable, insoluble product.

12. The assay of claim 11, including the further step of converting said stable, insoluble product to an activated form by illuminating it with light having a wavelength in the range of 340 nm to 380 nm.

13. The assay of claim 12, including the further step of illuminating the activated form of said product with light of a first wavelength, so that said activated product fluoresces at a second wavelength, longer than said first wavelength.

* * * * *